United States Patent [19]

Ruiz

[11] Patent Number: 5,980,945
[45] Date of Patent: Nov. 9, 1999

US005980945A

[54] SUSTAINED RELEASE DRUG FORMULATIONS

[75] Inventor: Jean-Marc Ruiz, Maintenon, France

[73] Assignee: Societe de Conseils de Recherches et d'Applications Scientifique S.A., Paris, France

[21] Appl. No.: 08/584,320

[22] Filed: Jan. 16, 1996

[51] Int. Cl.⁶ ........................................ A61K 9/08
[52] U.S. Cl. .................. 424/484; 514/2; 514/15; 514/16; 514/26; 514/169; 514/177; 514/182
[58] Field of Search ...................... 424/426, 408, 424/417, 418, 427, 451, 457, 484, 489, 491, 497; 514/2, 15, 16, 26, 169, 177, 182

[56] References Cited

U.S. PATENT DOCUMENTS

| | | | |
|---|---|---|---|
| 3,773,919 | 11/1973 | Boswell et al. | 424/19 |
| 4,678,809 | 7/1987 | Phillips | 514/599 |
| 4,707,470 | 11/1987 | Kirsch et al. | 514/31 |
| 4,767,628 | 8/1988 | Hutchinson | 424/426 |
| 4,938,763 | 7/1990 | Dunn et al. | 604/891.1 |
| 5,213,812 | 5/1993 | Ruiz | 424/499 |
| 5,470,582 | 11/1995 | Supersaxo et al. | 424/489 |
| 5,576,016 | 11/1996 | Amselem et al. | 424/450 |
| 5,582,591 | 12/1996 | Cheikh | 604/51 |
| 5,648,096 | 7/1997 | Gander et al. | 424/489 |

FOREIGN PATENT DOCUMENTS

| | | |
|---|---|---|
| 0 001 851 | 5/1979 | European Pat. Off. . |
| 0 21 847 A2 | 1/1981 | European Pat. Off. ......... A61K 9/00 |
| 0 503 583 A1 | 9/1992 | European Pat. Off. ....... A61K 47/36 |
| 04 018 035 | 1/1992 | Japan . |
| 08 143 449 | 6/1996 | Japan . |
| WO 85/00969 | 3/1985 | WIPO ............................ A61K 31/00 |
| WO 94/0862 | 4/1994 | WIPO ............................ A61K 47/24 |

OTHER PUBLICATIONS

Millest et al., "Sustained Release of Salmon Calcitonin In Vivo from Lactide: Glycolide Copolymer Depots", Calcif Tissue Int. 52:361–364, 1993.

*Primary Examiner*—Donna C. Wortman
*Assistant Examiner*—Brenda G. Brumback
*Attorney, Agent, or Firm*—John D. Conway; William McGowan; Fish & Richardson

[57] ABSTRACT

A sustained release drug formulation including: a drug; a biodegradable polymer which is insoluble in water; and an oil vehicle in which both the drug and the polymer are dissolved. The oil vehicle contains 10–100% by volume a pharmaceutically acceptable oil and 0–90% by volume a pharmaceutically acceptable liquid carrier for the drug or the polymer.

22 Claims, No Drawings

SUSTAINED RELEASE DRUG FORMULATIONS

BACKGROUND OF THE INVENTION

Biodegradable polymer sustained release formulations have been used to administer drugs over a prolonged period of time. See, e.g., U.S. Pat. Nos. 3,773,919 and 4,767,628. These formulations are generally in the form of solid cylindrical implants, microcapsules, or microspheres. Solid implants require incisions in the patient which often are quite painful, resulting in poor patient compliance. Solid microcapsules and microspheres, which are injected into the patient, are often difficult to reproducibly manufacture and, thus, can give varying release profiles. Also, microcapsules and microspheres require lyophilization in order to avoid agglomerization of the particles during storage and large needles for injection.

SUMMARY OF THE INVENTION

The invention features a sustained release drug formulation which includes: a drug; a biodegradable polymer insoluble in water (i.e., less than 0.01 mg/ml at 25° C.); and an oil vehicle containing 10–100% by volume a pharmaceutically acceptable and biodegradable oil and 0–90% by volume a pharmaceutically acceptable liquid carrier. The drug and the biodegradable polymer are dissolved in the oil vehicle.

The amount of a drug dissolved in an oil vehicle depends on its solubility, and may range from 1 to 500 mg per ml of the oil vehicle. The drug can be a peptide, e.g., somatostatin, luteinizing hormone-releasing hormone ("LHRH"), growth hormone releasing peptide, bombesin, gastrin releasing peptide, calcitonin, bradykinin, galanin, melanocyte stimulating hormone, growth hormone releasing factor, amylin, adrenomedullin, tachykinins, secretin, parathyroid hormone, enkephalin, endothelin, calcitonin gene releasing peptide, neuromedins, parathyroid hormone related protein, glucagon, neurotensin, adrenocorticotrophic hormone, peptide YY, glucagon releasing peptide, vasoactive intestinal peptide, pituitary adenylated cyclase activating peptide, motilin, substance P, neuropeptide Y, thyrotropin stimulating hormone, and analogs and fragments thereof. The drug can also be a steroid. Examples of a steroid drug include, but are not limited to, 17-β-hydroxy oestradiol and progesterone.

The drug can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), polymeric acids (e.g., tannic acid, carboxymethyl cellulose, polylactic, polyglycolic, or copolymers of polylactic-glycolic acids).

A suitable biodegradable polymer to be used to practice this invention is a polyester. Examples of monomers used to form such a polyester include, but are not limited to, ε-caprolactone, lactic acid, glycolic acid, ε-caprolic acid, p-dioxanone, ε-caprionic acid, 1,5-dioxepan-2-one, 1,4-dioxepan-2-one, alkylene oxylate, cycloalkylene, cycloalkylene oxylate, alkylene succinate, and 3-hydroxy butyrate,. Note that any optically active isomers or racemates can be used. Further, the polyester can be a copolymers prepared from two or more different monomers.

The biodegradable polymer may be a liquid, or have a glass transition temperature or a melting temperature up to 200° C. It may have a molecular weight (averaged) of 500–150,000 daltons, preferably, 1,000–75,000 daltons. Polymers with higher molecular weights slow down the release of the drug from the formulation. Generally speaking, 1–500 mg (preferably, 15–300 mg) of the polymer can be dissolved in 1 ml of the oil vehicle.

Examples of a biodegradable oil, an essential component of the oil vehicle, include oils derived from plants (e.g., corn oil, coconut oil, linseed oil, olive oil, palm oil, sunflower seed oil, cottonseed oil, peanut oil, sesame oil, or castor oil), animals (e.g., sardine oil, codliver oil, whale oil, sperm oil), paraffin oil, or triglyceride derivatives such as miglyol (Labafac, Gattefusse, Lyon, France), or mixtures thereof.

The oil vehicle may also contain one or more pharmaceutically acceptable liquid carriers, e.g., solvents of either the drug or the polymer such as water and ethanol. The amount of a carrier added should remain miscible with the oil used to form the vehicle. If necessary, a pharmaceutically acceptable liquid ester or polyether may be added to the oil vehicle to aid in the dissolution of the drug or the polymer into the oil vehicle. Examples of suitable esters include benzyl benzoate (which can assist the dissolution of the polymer such as a polyester), or polyethylene glycol, e.g., PEG 400 (which can assist the dissolution of the drug such as a peptide). The ester or polyether may constitute 0.1–90% by volume of the oil vehicle.

The oil vehicle may also include a pharmaceutically acceptable surfactant in order to clarify the formulation. Examples of suitable surfactants include polysorbates (e.g., TWEEN 80 or SPAN 80).

Thus, what is meant by "an oil vehicle" herein is a water-immiscible medium in which a drug and a biodegradable polymer are dissolved. It contains at least an oil and may also contain a liquid carrier for the drug or polymer, a liquid ester or polyether, or a surfactant.

Sterilization of formulations may be assured by microfiltration. This specialized technique, which is for low viscosity liquid formulations labile to heat or other sterilization methods, depends upon the physical removal of microorganisms by adsorption onto a filter or sieve mechanism. The separation of microorganisms from the filtrate may involve interactions associated with electrostatic forces or mechanical sieving by the size, shape, and tortuousness of the voids. Examples of filters for achieving sterility have a nominal porosity of 0.22 μm. The formulations of the invention may be stored at 4° C. sheltered from sunlight.

The formulations of the present invention may be distributed into the systemic circulation by parenteral, e.g., intramuscular or subcutaneous, administration, oral, ophthalmic, nasal, or pulmonary administration.

Other features and advantages of the present invention will be apparent from the detailed description of the invention, and also from the claims.

DETAILED DESCRIPTION OF THE INVENTION

It is believed that one skilled in the art can, based on the description herein, utilize the present invention to its fullest extent. The following specific examples, which shows various ways of preparing and testing several formulations of this invention are therefore to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

EXAMPLE 1

In a 100 ml beaker, 6 ml of benzyl benzoate and 8 ml of polyethylene glycol 400 (PEG 400) were mixed together. 6 ml of sesame oil was then added to and mixed within the beaker, forming an oily substance. The oily substance was then mixed with 50 mg of a biodegradable polymer and was added to the same beaker and dissolved by heating the beaker to 60° C. while stirring. The beaker was then cooled. 10 mg of blue patente V dye (Prolabo, Fontenay Sous, Bois, France; used here as a drug substitute for experimental purposes) dissolved in 0.1 ml of water and 0.1 mg of TWEEN 80 dissolved in 0.9 ml of ethanol were mixed with the oily substance to form the sustained release formulation. The biodegradable polymer was a copolymer comprising 50% by weight D,L-lactic acid and 50% by weight glycolic acid ("50/50 PLGA") and having an average molecular weight between 20,000 and 30,000 daltons, and was synthesized using standard methods known in the art. See, e.g., U.S. Pat. Nos. 2,703,316 or 2,758,987.

2 ml of the resulting sustained release formulation was poured into a vial containing 20 ml of distilled water. The oil settled at the bottom of the vial and formed an emulsion. Upon agitation with a magnetic stirrer, the emulsion formed globules. The blue dye remained in the emulsion globules and was slowly released into the surrounding water over time. The subsequent addition of 3 ml of methylene chloride to the vial, a solvent of the copolymer, degraded the emulsion and quickly release the blue dye into the distilled water.

EXAMPLE 2

The formulation prepared by the procedures described above in Example 1 was poured into a vial containing 20 ml of saline. Again, the dye was contained within the congealed globules, and was slowly released into the surrounding saline upon the addition of 3 ml of methylene chloride.

EXAMPLE 3

8 ml of PEG 400 and 6 ml of benzyl benzoate were added to and mixed within a 100 ml beaker. 500 mg of 50/50 PLGA copolymer having an average molecular weight of 30,000 to 40,000 was added to the same beaker and dissolved by heating the beaker to 60° C. while stirring. The beaker was then cooled. 51 mg of the water-soluble acetate salt of the LHRH agonist Triptorelinl™ (p-Glu-His-Trp-Ser-Tyr-D-Trp-Leu-Arg-Pro-Gly-$NH_2$) was dissolved in a solvent consisting of 0.1 ml of water and 0.9 ml of ethanol, and the resulting solution was then added to and mixed within the beaker. 6 ml of castor oil was then slowly added to and mixed within the same beaker. Finally, 100 µl of ethanol was added to and mixed within the same beaker in order to clarify the resulting formulation.

The formulation was dispersed into a vial containing distilled water, and the vial was agitated. The formulation emulsified as globules in the vial. The globules had a mean diameter of 60 nM. High performance liquid chromatography revealed virtually no degradation of the LHRH agonist during the formulation process.

EXAMPLE 4

The formulation described in Example 3 was injected into Wistar rats (IFFA Credo, St. Germain Sur L'Arbesle, France) at a dose of 400 µg of peptide per kg weight of rat. Plasma levels of testosterone (ng/ml) were determined from blood samples collected at different days by sinus retroorbital taking. 50 µl of blood sample, 200 µl of $I^{125}$ testosterone, and 200 µl of antiserum were poured into tubes which were shaken and incubated during 24 hours at 37° C. The immuno-precipitant reagent propanol (1 ml) was added in each tube, and all the tubes were incubated 15 minutes at room temperature. The supernatant was eliminated after centrifugation, and radioactivity was measured with a multigamma counter LKB-WALLAC Model 1261 (LKB, Les Ulis, France).

The data is presented in Table I. As the data indicated, the formulation continuously release the LHRH agonist over a period of at least 29 days as indicated by the inhibition of testosterone in the rats.

TABLE I

| DAYS | TESTOSTERONE (ng/ml) |
|---|---|
| 0 | 2.80 |
| 2 | 4.17 |
| 4 | 0.47 |
| 8 | 0.64 |
| 11 | 1.34 |
| 15 | 1.04 |
| 18 | 0.69 |
| 22 | 1.63 |
| 25 | 1.57 |
| 29 | 0.85 |

EXAMPLE 5

The above synthetic protocol in Example 3 was performed with the exception that 62 mg of the insoluble pamoate salt of Triptorelinl™ dissolved in 1 ml of ethanol was used instead of 51 mg of the acetate salt of Triptorelinl™ dissolved in 0.1 ml of water and 0.9 ml of ethanol. The resulting formulation was injected into Wistar rats at a concentration of 400 µg/kg as performed in Example 4. The data is presented in Table II. The formulation slowly released the LHRH agonist over a period of at least 17 days.

TABLE II

| DAYS | TESTOSTERONE (ng/ml) |
|---|---|
| 0 | 2.50 |
| 2 | 3.33 |
| 3 | 1.30 |
| 7 | 0.68 |
| 10 | 0.84 |
| 14 | 0.29 |
| 17 | 0.46 |

EXAMPLE 6

8 ml of PEG 400 and 6 ml of benzyl benzoate were added to and mixed within a 100 ml beaker. 50 mg of a 50/50 PLGA copolymer was then added to the same beaker and dissolved by heating the beaker to 60° C. while stirring. 90 percent, by weight, of the copolymer, had an average molecular weight of 20,000 to 30,000 while 10 percent, by weight, of the copolymer had an average molecular weight of 1500 to 2000. The beaker was then cooled. 388 mg of the pamoate salt of the somatostatin agonist LANREOTIDE (D-Nal-c[Cys-Tyr-D-Trp-Lys-Val-Cys]-Thr-$NH_2$) was dissolved in 1 ml of ethanol, and the resulting solution was added to and mixed within the same beaker. Finally, 6 ml of castor oil was then slowly added to the same beaker to form the sustained release formulation.

EXAMPLE 7

The formulation described in Example 6 was intramuscularly injected into Wistar rats at a dose of 6 mg of peptide per kg weight of rat. Blood for peptide analysis was collected into aprotinine tubes to avoid any peptide degradation (Laboratoire CHOAY, Gentilly, France). Samples were centrifuged immediately and the plasma separated and stored at −20° C. until radioimmunoassay ("RIA") to determine the amounts of the drug (ng/ml). RIA had been developed after immunization of rabbits with peptide conjugated to bovine serum albumin to obtain a specific antibody. Iodine 125 has been used to label LANREOTIDE.

The data is presented in Table III. The formulation slowly released LANREOTIDE over a period of at least 12 days.

TABLE III

| DAYS | LANREOTIDE (ng/ml) |
| --- | --- |
| 2 | 9.31 |
| 5 | 1.87 |
| 8 | 0.81 |
| 12 | 0.28 |

EXAMPLE 8

The above synthetic protocol in Example 6 was performed with the exception that 365 mg of the acetate salt of LANREOTIDE dissolved in 0.1 ml of water and 0.9 ml of ethanol was used instead of 388 mg of the pamoate salt of LANREOTIDE dissolved in 1 ml of ethanol. This formulation was injected into Wistar rats at a dose of 6 µg/kg and RIA performed in the manners as described in Example 7. The data is presented in Table IV. The formulation slowly released the peptide over a period of at least 14 days.

TABLE IV

| DAYS | LANREOTIDE (ng/ml) |
| --- | --- |
| 2 | 26.14 |
| 5 | 3.15 |
| 8 | 0.79 |
| 12 | 0.37 |
| 14 | 0.16 |

EXAMPLE 9

10 ml of PEG 400 and 8 ml of benzyl benzoate were added to and mixed within a 100 ml beaker. 1 g of 50/50 PLGA copolymer having an average molecular weight of 40,000 to 50,000 was added to the same beaker and dissolved by heating the beaker to 60° C. while stirring. The beaker was then cooled. 200 mg of the steroid 17β-hydroxy-φestradiol was then added to and mixed within the beaker. 4 ml of castor oil was then slowly added to and mixed within the same beaker.

EXAMPLE 10

The formulation described in Example 9 was intramuscularly injected into Wistar rats at a dose of 4 mg/kg. The concentration of the steroid was determined using an EIA (enzymoimmunoassay) kit (Cayman Chemical, SPI-BIO, Massay, France). The data is presented in Table V. The formulation slowly released the 17β-hydroxy-φestradiol over a period of at least 11 days.

TABLE V

| DAYS | 17β-HYDROXY-OESTRADIOL (ng/ml) |
| --- | --- |
| 2 | 12.45 |
| 4 | 2.62 |
| 8 | 0.19 |
| 11 | 0.10 |

EXAMPLE 11

10 ml of PEG 400 and 8 ml of benzyl benzoate were added to and mixed within a 100 ml beaker. 1 g of 50/50 PLGA copolymer having an average molecular weight of 40,000 to 50,000 was then added to the same beaker and dissolved by heating the beaker to 60° C. while stirring. The beaker was then cooled. 200 mg of progesterone was then added to and mixed within the beaker. 4 ml of castor oil was then mixed with 2 ml of ethanol and slowly added to the same beaker to form the sustained release formulation.

EXAMPLE 12

The formulation in Example 12 was injected into Wistar rats at a dose of 4 µg/kg. The concentration of the steroid (ng/ml plasma) was determined using an EIA kit (Cayman Chemical, SPI-BIO, Massay, France). The data is presented in Table VI. The formulation slowly released progesterone over a period of at least 11 days.

TABLE VI

| DAYS | PROGESTERONE (ng/ml) |
| --- | --- |
| 2 | 11.54 |
| 4 | 9.51 |
| 8 | 1.39 |
| 11 | 1.97 |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A sustained release drug formulation, said formulation comprising:

a drug;

a biodegradable polymer which is insoluble in water; and an oil vehicle containing a pharmaceutically acceptable oil which is biodegradable and a pharmaceutically acceptable liquid carrier which dissolves said drug or said polymer, said oil vehicle comprising 10–100% by volume of said oil and 0–90% by volume of said liquid carrier;

wherein both said drug and said polymer are dissolved in said oil vehicle, provided that said polymer is not over 75,000 daltons.

2. A formulation of claim 1, wherein the amount of said polymer is 1–500 mg per ml of said oil vehicle.

3. A formulation of claim 2, wherein the amount of said polymer is 15–300 mg per ml of said oil vehicle.

4. A formulation of claim 3, wherein the molecular weight of said polymer is 1,000–75,000 daltons.

5. A formulation of claim 4, wherein said oil is corn oil, cottonseed oil, peanut oil, sesame oil, castor oil, or a mixture thereof.

6. A formulation of claim 1, wherein said polymer is made of a monomer selected from $\epsilon$-caprolactone, lactic acid, glycolic acid, and a combination thereof.

7. A formulation of claim 6, wherein the molecular weight of said polymer is 1,000–75,000 daltons.

8. A formulation of claim 7, wherein said oil is corn oil, cottonseed oil, peanut oil, sesame oil, castor oil, or a mixture thereof.

9. A formulation of claim 1, wherein said oil is corn oil, cottonseed oil, peanut oil, sesame oil, castor oil, or a mixture thereof.

10. A formulation of claim 1, wherein said oil vehicle further comprises a pharmaceutically acceptable ester or polyether to facilitate dissolution of said drug or polymer, said ester or polyether constituting 0.1–90% by volume of said oil vehicle.

11. A formulation of claim 10, wherein said ester or polyether is benzyl benzoate, polyethylene glycol, or a mixture thereof.

12. A formulation of claim 11, wherein said oil vehicle further comprises a pharmaceutically acceptable surfactant.

13. A formulation of claim 10, wherein said oil vehicle further comprises a pharmaceutically acceptable surfactant.

14. A formulation of claim 1, wherein said oil vehicle further comprises a pharmaceutically acceptable surfactant.

15. A formulation of claim 1, wherein said drug is a peptide.

16. A formulation of claim 15, wherein said peptide is a somatostatin agonist or an LHRH agonist.

17. A formulation according to claim 16 wherein the LHRH agonist is p-Glu-His-Trp-Ser-Tyr-D-Trp-Leu-Arg-Pro-Gly-$NH_2$.

18. A formulation according to claim 16 wherein the somatostatin agonist is D-Nal-c[Cys-Tyr-D-Trp-Lys-Val-Cys]-Thr-$NH_2$.

19. A formulation according to claim 15 wherein the peptide is selected from the group consisting of growth hormone releasing peptide, bombesin, gastrin releasing peptide, calcitonin, bradykinin, galanin, melanocyte stimulating hormone, growth hormone releasing factor, amylin, adrenomedullin, tachykinins, secretin, parathyroid hormone, enkephalin, endothelin, calcitonin gene releasing peptide, neuromedins, parathyroid related protein, glucagon, neurotensin, adrenocorticotrophic hormone, peptide YY, glucagon releasing peptide, vasoactive intestinal peptide, pituitary adenylated cyclase activating peptide, motilin, substance P, neuropeptide Y and thyrotropin stimulating hormone, or an analog or fragment thereof.

20. A formulation of claim 1, wherein said drug is a steroid.

21. A formulation of claim 20, wherein said steroid is 17-$\beta$-hydroxy $\phi$estradiol or progesterone.

22. A method of administering to a patient a formulation according to claim 1, comprising administering said formulation parenterally.

* * * * *